United States Patent [19]
Kouvonen et al.

[11] Patent Number: 5,712,170
[45] Date of Patent: Jan. 27, 1998

[54] TEST STRIP, ITS PRODUCTION AND USE

[75] Inventors: Ilkka Sakari Kouvonen, Kauniainen; Eivor Helena Svens, Espoo; Sari Hannele Tikanoja, Helsinki; Pekka Antero Turunen, Joensuu; Lauri Markus Sivonen, Helsinki, all of Finland

[73] Assignee: Oy Medix Biochemica AB, Kauniainen, Finland

[21] Appl. No.: 335,755

[22] PCT Filed: Dec. 29, 1993

[86] PCT No.: PCT/FI93/00569

§ 371 Date: Nov. 14, 1994

§ 102(e) Date: Nov. 14, 1994

[87] PCT Pub. No.: WO94/15215

PCT Pub. Date: Jul. 7, 1994

[30] Foreign Application Priority Data

Dec. 29, 1992 [FI] Finland ................... 925922

[51] Int. Cl.$^6$ .................. G01N 33/543; G01N 33/558
[52] U.S. Cl. .................. 436/518; 422/56; 422/57; 422/58; 435/4; 435/287.1; 435/287.2; 435/287.7; 435/287.9; 435/805; 435/810; 435/970; 435/971; 435/973; 436/169; 436/510; 436/514; 436/528; 436/531; 436/805; 436/810
[58] Field of Search .................. 422/50, 55, 56, 422/57, 58, 68.1; 435/4, 7.1, 805, 970, 971, 973, 287.1, 287.2, 287.7, 287.9, 810; 436/510, 518, 523, 528, 531, 536, 164, 906, 514, 805, 810, 169

[56] References Cited

U.S. PATENT DOCUMENTS

| 4,094,647 | 6/1978 | Deutsch et al. ............ 23/253 TP |
| 4,169,138 | 9/1979 | Jonsson ............ 424/12 |
| 4,592,893 | 6/1986 | Poppe et al. ............ 422/56 |

(List continued on next page.)

FOREIGN PATENT DOCUMENTS

| 0 007 654 | 2/1980 | European Pat. Off. ....... G01N 33/58 |
| 0 032 270 A1 | 7/1981 | European Pat. Off. ....... G01N 33/58 |

(List continued on next page.)

OTHER PUBLICATIONS

Hudson, L. and Hay, F.C., *Practical Immunology*, Second Edition Blackwell Scientific Publications, (1983) pp. 1–23.

Stenman, U–H., et al., "Characterization of a Monoclonal Antibody to Human Alpha–Fetoprotein and its Use in Affinity Chromatography," *J. Immunol. Methods* 46:337–345 (1981).

Van Regenmortel, M.H.V., et al., "Synthetic Polypeptides As Antigens," Chap. 3 *Lab. Techn. in Biochem. and Mol. Biol.* 19:95–130, ed. Burdon, R.H., Elsevier, New York (1988).

Dialog File 351 (World Patent Index), English Abstract of DE 39 41 150 A1.

Dialog File 351 (World Patent Index), English Abstract of EP 174,247.

Dialog File 351 (World Patent Index), English Abstract of EP 186,799.

Dialog File 351 (World Patent Index), English Abstract of EP 520,202.

*Primary Examiner*—Christopher L. Chin
*Attorney, Agent, or Firm*—Birch, Stewart, Kolasch & Birch, LLP

[57] ABSTRACT

A test strip for a rapid immunoassay containing specific immunochemical reagent zones (7, 8, 9) is described. The test strip (10) has a backing sheet (1) and attached thereto a receiving end pad (3) and at a distance therefrom a finishing end pad (5). A test membrane (2) is provided between said pads (3, 5). Said membrane (2) is positioned in parallel relationship to said backing (1) at a distance therefrom so that said backing (1) and said membrane (2) limit between themselves an air gap (4) which is open at its edges. Said gap (4) functions as a sheltered reaction chamber for the immunolgical reaction taking place as a liquid is made to flow through said membrane (2). The test strip is simple to manufacture by lamination and easy to use and it is suitable for both diagnostic and environmental immunoassays.

14 Claims, 1 Drawing Sheet

U.S. PATENT DOCUMENTS

| | | | |
|---|---|---|---|
| 4,861,711 | 8/1989 | Friesen et al. | 436/7 |
| 5,104,811 | 4/1992 | Berger et al. | 436/164 |
| 5,141,850 | 8/1992 | Cole et al. | 436/525 |
| 5,296,353 | 3/1994 | Ochoa et al. | 435/7.23 |
| 5,384,264 | 1/1995 | Chen et al. | 422/56 |
| 5,411,858 | 5/1995 | McGeehan et al. | 435/805 |
| B1 4,366,241 | 10/1988 | Tom et al. | 435/7 |

FOREIGN PATENT DOCUMENTS

| | | | |
|---|---|---|---|
| 0 063 810 A1 | 4/1982 | European Pat. Off. | G01N 33/54 |
| 0 088 636 A2 | 9/1983 | European Pat. Off. | G01N 33/52 |
| 0 149 168 A1 | 7/1985 | European Pat. Off. | G01N 33/543 |
| 0 154 749 A1 | 9/1985 | European Pat. Off. | G01N 33/548 |
| 0 170 746 A1 | 2/1986 | European Pat. Off. | G01N 33/543 |
| 0 174 247 B1 | 3/1986 | European Pat. Off. | G01N 33/548 |
| 0 183 442 A3 | 6/1986 | European Pat. Off. | G01N 33/52 |
| 0 186 799 B1 | 7/1986 | European Pat. Off. | G01N 33/52 |
| 0 191 640 A2 | 8/1986 | European Pat. Off. | G01N 33/52 |
| 0 225 054 A1 | 6/1987 | European Pat. Off. | G01N 33/52 |
| 0 250 137 A2 | 6/1987 | European Pat. Off. | G01N 31/558 |
| 0 291 194 B1 | 11/1988 | European Pat. Off. | G01N 33/543 |
| 0 421 294 A3 | 4/1991 | European Pat. Off. | G01N 33/543 |
| 0 520 202 A3 | 12/1992 | European Pat. Off. | G01N 33/558 |
| 39 41 150 A1 | 6/1991 | Germany | G01N 33/535 |
| 2 016 687 | 9/1979 | United Kingdom | G01N 33/16 |
| 1 589 234 | 5/1981 | United Kingdom | G01N 31/52 |
| 2 204 398 | 11/1988 | United Kingdom | G01N 33/532 |
| WO 86/04683 | 8/1986 | WIPO | G01N 33/543 |
| WO 87/02774 | 5/1987 | WIPO | G01N 3/52 |
| WO 92/01226 | 1/1992 | WIPO | G01N 33/558 |

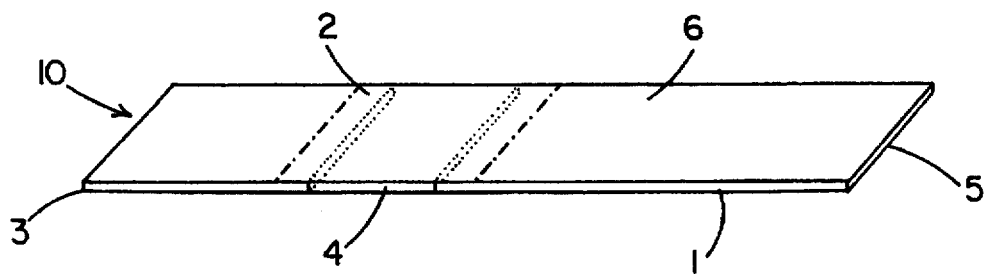
FIG. IA
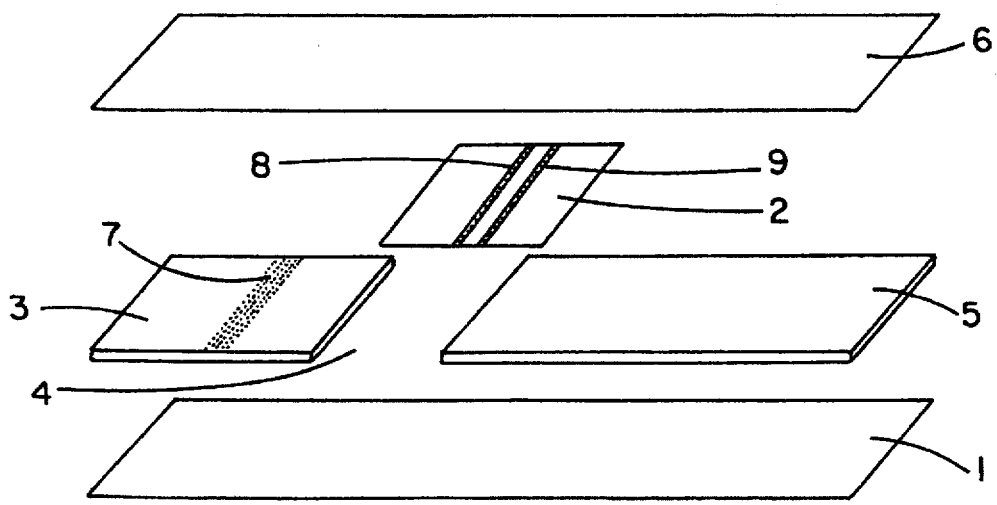
FIG. IB
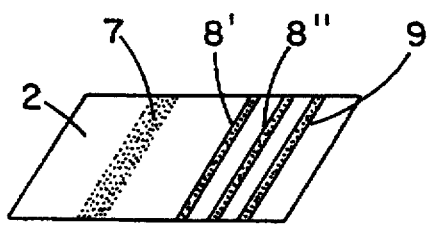
FIG. 2
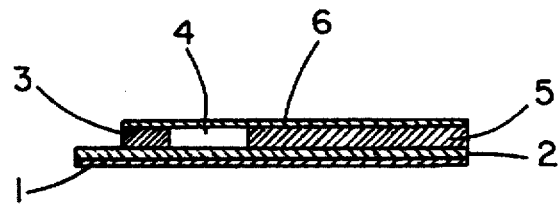
FIG. 3

TEST STRIP, ITS PRODUCTION AND USE

The present invention concerns a test strip providing a rapid immunoassay which does not require separate reagents, apparatuses or devices. An assay may be performed simply by dipping a certain area of said test strip in a liquid sample and by observing a visible change in said strip taking place within a short space of time as a result of an immunological reaction. The present invention also concerns an advantageous industrial method for producing said test strip as well as its use in diagnostic and environmental analytical determinations.

Immunoassays are based on the use of antibodies. Antibodies comprise biologically provided reagents which bind to a desired analyte with great specificity. Immunoassays have been developed largely for clinical medicine wherein their sensitivity and specificity is of great value. There exist, however, good possibilities for immunoassays to serve also in environmental analysis by offering reliable assays for detecting pollutants in air, water and soil, for food quality control, etc.

The need for analysis of various environmental pollutants has increased in recent times. There is a need to find out the amount of pollutants, in order to assess whether the environment in question is potentially dangerous to men or animals. There is, for instance, a need to analyse whether the ground around service stations contains remnants of fuel containing various carcinogens; whether there are pathogenic bacteria in drinking water; whether there are carcinogenic remnants of pesticides in vegetables; whether there are remnants of chemicals preventing decomposition or slime formation in waste waters of wood industry, etc. When an environment has been found to be polluted, there is also a need to monitor the cleaning process by analysis. Further, new pollutions may be prevented by studying the dosage of toxic chemicals by analysis. In several fields there exists legislation on maximal concentrations of potentially harmful compounds, as well as various recommendations, which also requires reliable methods of analysis.

Since the compounds to be studied in the environment are so numerous, there is a great variation in the present methods of analysis. Bacteria are detected by microbiological cultivation and identification methods. For other pollutants traditional methods of analytical chemistry are used. Many carcinogenic compounds, for instance pesticides, are small molecules containing aromatic rings and these are well suited for gas chromatographic analysis. The analyses are often preceded by complex extraction processes. In some cases, determinations of bioassay type are in use (for instance, algal toxins are detected by studying the effect of a sample on mice).

Said analyses very often require complicated equipment and most analytical methods are badly suited to being performed in large series. This raises the costs of the determinations and prevents testing as many samples as actually needed. Only very few determinations of a general nature (such as the pH of water or a soil sample, or the detection of certain heavy metals) can be performed at the sampling site using rapid tests.

As examples of rapid tests which have long been used in clinical chemistry, tests for urinary pH, glucose and protein may be mentioned. The test means comprise strips that are dipped into a sample and interpreted according to color models on the package. Color changes are usually based on pH indicators or specific enzymatic reactions.

Immunochemical methodology was long considered to be expensive and complicated to perform, and it was used only for the most demanding determinations. During the last few years, however, rapid immunochemical tests have been developed for the needs of clinical chemistry. Said tests can be performed by an untrained person in a few minutes without any special equipment, the result being visually readable. This technique has been applied especially to pregnancy tests suitable for home use.

The most usual technical version of this kind of rapid test is disclosed in Patent publication GB 2204398B, the diagnostic test of which is based on two antibodies. One of them is attached to a nitrocellulose membrane in the form of a line. The other one is attached to the surface of colored latex or gold colloid particles dried onto the same membrane. The test is performed by absorbing a liquid sample into said membrane. The particles are freed by the liquid flow and the analyte to be determined binds to the antibody on said particles. By another molecular site said analyte binds also to the other antibody which is present in said line, and a visible colored line is formed to show the presence of said analyte. This kind of immunochromatographic test technique that is based on a flow on a membrane, is often called "lateral flow technique".

The above technique may also be used in semiquantitative or quantitative analysis. If the analyte molecule is so small that the simultaneous binding of two antibodies is not possible, a competitive principle may be used, where only one antibody is used and in addition thereto a labeled analyte. In this case, the presence of the analyte in the sample is shown by, for instance, the absence of a colored line.

In an immunochemical rapid test disclosed in U.S. Pat. No. 5,141,850 a sample is absorbed into a porous test membrane having two zones with mobile antibody reagents. One of said reagents is labeled with a signal producing label. A third, immobile zone contains a substance capable of catching the non-signal producing antibody. If the sample contains the antigen to be tested, both antibodies bind to said antigen and the complex is in turn bound to the immobile catching substance, causing color formation.

Other simple immunochemical test devices are described, among others, in the following Patent publications: PCT/EP86/00055, where an enzyme immunological principle is applied and, thus, separate reagents are needed; GB 1 589 234 A and EP 0225 054 A1, where an enzyme immunological reaction is started after sample addition by dipping one end of a strip into a developing solution; EP 0 186 799 B1, where the structure comprises overlapping strips containing reagents that dissolve in the sample liquid; EP 0 421 294 A2, which describes the use of a selenium colloid in the lateral flow principle and has test and control antibodies coated as a "plus" figure on the membrane; EP 0 149 168 B1, where the reaction takes place in a glass capillary tube in layers of a chromatographic carrier substance.

The prior art references mentioned above describe the use of immunochemical tests in diagnostics. EP Patent publication 0 520 202 A2, on the other hand, describes an immunochemical test that is especially intended for the analysis of environmental pollutants. The analyte to be tested migrates into a reaction layer containing a label-antibody complex, where said analyte is able to displace said label and bind instead in said layer. The detached label migrates through the reaction layer into another layer that is transparent and the concentration can be directly detected visually.

A rapid diagnostic test is described in U.S. Pat. No. 5,104,811 as involving an absorbent pad attached to a strip-like backing and at least one immunochemical reaction layer attached at a short distance from said pad. Migration of liquid from the pad to the reaction layer is carried out either in a fibrous transfer layer or in a capillary gap between the reaction layer and the backing, said gap being closed at its edges.

As the use of tests is increasing worldwide, there is a growing need to develop tests that are so simple that they can be performed, not only in well equipped laboratory conditions, but also nearly anywhere else, for instance at home, in factory or field conditions, even without electricity or clean water. It should be possible even for an untrained person to perform the test. Test performance should be rapid, sensitive and reliable. Test construction should be simple enough to allow manufacturing without complicated methods. The test strip should, however, also be strong enough to withstand environmental field conditions.

The present invention provides a test strip having a structure which is simple and advantageous in view of manufacture. A test may be performed simply by dipping the test strip into sample and observing the result. In spite of the strip-like shape of the test device, the essential reactions take place at a protected chamber-like gap. The laminated structure of the test strip also enables an advantageous industrial manufacturing and packaging method.

The test strip according to the present invention is described in more detail in the following specification and in the Figures illustrating the invention. The specific features of the invention are defined in the appended claims.

Thus, the object of the present invention is a test strip for a rapid immunoassay containing specific immunochemical reagent zones, said test strip having a backing sheet and attached thereto a receiving end pad and at a distance therefrom a finishing end pad. A test membrane is provided between said pads. Said membrane is intended for being brought into liquid flow contact with a sample either directly or via said receiving end pads. Said membrane is positioned in parallel relationship to said backing at a distance therefrom. Said test strip is characterized in that said backing and said membrane limit between themselves an air gap which is open at its edges. Said chamber will function as a sheltered reaction chamber for the immunological reaction taking place in said membrane.

The test strip preferably has two supporting covers or backings, one on either side. One of said backings is advantageously at least partly transparent, thus enabling the color formation on the test membrane to be seen.

The pads between backing and test membrane are advantageously absorbing pads and especially, the absorbing pad at the receiving end is extended beyond the test membrane so that a liquid sample can be made to flow via the absorbing pad into the test membrane. Since said pad is made of a porous material, it will act as a filter retaining solid impurities possibly present in non-homogeneous samples. A continuous liquid flow through the reaction zones in the test strip may be ensured by using an absorbent material as the pad also at the finishing end.

The test membrane preferably carries a test zone containing an immobile reagent and a control zone containing control substance. A label zone containing a mobile label is applied to the test membrane or into the absorbing pad at the receiving end, thus enabling the label to migrate to the test zone carried by liquid flow. The strip may also contain a mobile but unlabeled reagent. In that case, the test zone contains a substance capable of catching said reagent. There may be more than one test membrane in the same strip in order to test different analytes, or the same membrane may contain more than one zone each containing different reagents. The strip may also contain several different concentrations of the same reagent or label, in order to determine different analyte concentrations semiquantitatively.

The present invention also relates to a continuous industrial manufacturing process providing an especially advantageous method for producing a test strip. In the manufacturing method according to the invention, one or more label compounds or/and test substances specific to the immunochemical reaction are dispensed as reagent zones along the full length of the test membrane material. The zones are separate and longitudinally continuous. Advantageously, one further narrow zone containing a control substance is dispensed on the membrane material next to the zone containing test substance. The dispensed zones are thereafter dried. At least two strings of pad material are attached at a distance from each other on a separate long backing support material. One of the pad material strings may contain one or more immunochemical reagents that have been dried therein beforehand. The length of test membrane that has been prepared as described above is placed on the pad material strings so that the reagent zones are facing the gap between said pads. Transparent covering support material of at least the size of the backing support material is attached on top of the test membrane and the pad strings, thus providing a long laminated test strip blank that can be cut into test strips of desired size.

The present invention also relates to the use of the test strip for a rapid immunoassay in diagnostics and in environmental analysis.

The following represents a more detailed description of the invention with reference to the appended figures wherein FIG. 1A is a perspective view of a preferred embodiment of the test strip according to the invention;

FIG. 1B shows an exploded view of the separate parts of the embodiment according to FIG. 1;

FIG. 2 shows a test membrane to be used in the test strip according to the invention and the zones according to one of its embodiments;

FIG. 3 shows a schematic cross section of another embodiment of the test strip according to the invention.

FIGS. 1A and 1B show a preferred embodiment of the test strip according to the present invention. The back side of the test strip, generally indicated by reference numeral 10, is formed by a backing 1 made of plastic or some other suitably stiff material. Both ends of said backing 1 are provided with relatively thin pads 3, 5. Said pads are preferably made of a material that has a high absorbing capacity and is chemically inert. Pad 3 at the receiving end may be treated with various substances in order to increase its absorbing capacity and to increase the speed of liquid flow therein. A zone 7 in absorbing pad 3 contains a dried labeled reagent. Test membrane 2, which is where the actual reaction to be detected will take place, is placed on and between absorbing pads 3 and 5.

Absorbing pads 3 and 5 are separated by a gap 4 which is long enough to extend over the reaction area in test membrane 2, i.e. the area containing the reaction zone or zones. The zones at gap 4 comprise at least one specific antibody line 8, as well as any control line(s) 9. When test strip 10 is manufactured, membrane 2 is placed on top of pads 3 and 5 in such a way that the exposed reactive test side of membrane 2 is facing gap 4. The contact area between membrane 2 and pads 3 and 5, respectively, must be large enough to create and maintain a liquid flow.

The above arrangement results in a structure, wherein the reaction surface in test membrane 2 is not in contact with any material. Instead there is a gap 4 between membrane 2 and backing 1, which gap can be described as a small chamber, open on both sides, where the liquid flow on membrane 2 is undisturbed. Absorbing pads 3 and 5 are advantageously approximately 0.5–3 mm thick so that gap 4 will be narrow. Since gap 4 is narrow, the atmosphere in the gap 4 retains its humidity and any drying caused by air draught will not disturb the flow of liquid.

Another backing, namely a cover 6 is advantageously attached on top of membrane 2 and pads 3, 5. The said cover 6 may be a transparent sheet preferably of the same size as test strip 10 and made, for instance, of clear plastic like PVC, PE or PC. Said cover protects membrane 2 and pads 3, 5, keeps liquids from evaporating, and strengthens the structure. Because cover 6 is transparent, the test result will be visible in spite thereof. The cover may be painted in a suitable way or it may be provided with a tape or tapes (not shown) which facilitate interpretation of the test by covering the other parts of said strip except the area, where the test lines are formed. Cover 6 may also be made of non-transparent material with an opening or openings cut therein to enable the test result to be seen. Alternatively, backing 1 will be transparent and the reaction can be observed through gap 4.

FIG. 2 presents another embodiment of the reagent zones where all the zones have been dispensed on test membrane 2. Reference numeral 7 indicates a zone wherein particles used as label have been dried on a layer of a dried sugar solution; zones 8' and 8" contain antibodies specific to two different analytes; and zone 9 has control antibody attached to it.

The test is based on the lateral flow principle. Thus, the reaction occurs on membrane 2, the chemical properties of which are chosen so as to make it possible to apply thereto antibodies and other substances needed in the reaction. Said membrane should be porous in a way suitable to create a liquid flow therein and to enable the substances needed for detection (e.g. latex, metal colloid or other particles as well as soluble molecules) to be carried by said flow. A suitable material for test membrane 2 is nitrocellulose. Said membrane may alternatively be made of nylon or some other suitable material.

If test membrane 2 is very thin, it is advantageous to attach it to a support of its own (not shown in Figs.). This will facilitate its treatment during the coating processes that precede test assembly. If detection of the reaction is to be viewed on the side having said membrane support, said support should be transparent.

The number and position of zones on test membrane 2 can vary depending on the analyte to be tested. The same membrane may contain several reagents for detecting different analytes in the same sample or correspondingly, for detecting different concentrations of the same analyte. The strip may also include several test membranes. In such a case there must be an uninterrupted flow between them, which may be achieved, for instance, by placing said membranes at least partly on top of each other or by arranging a porous interconnecting membrane between them.

Using a test strip in accordance with the present invention it is possible to perform a test, for example a pregnancy test, a Listeria test of food or an atrazine test in water, by placing the receiving end of strip 10 up to a certain level into the sample or an extract of the original sample. Liquid will be absorbed into pad 3 at said receiving end, from where it will migrate further to test membrane 2. Control line 9 will become visible as soon as the liquid flow has reached said line. When the test is based on an immunometric principle the test is positive if another, specific test line has also become colored.

FIG. 3 presents an alternative embodiment of the test strip according to the present invention, wherein backing 1 carries the porous test membrane 2. At a certain distance from a receiving end of said membrane there is an inert supporting pad 3. Another supporting pad 5 is attached to the opposite end of the membrane-backing combination so that an empty space remains between pads 3 and 5. On top of pads 3 and 5 a cover 6 is attached to cover said pads in a way that results in the formation of a gap 4 which is open at its edges. Either backing 1 or cover 6, or both are made of a transparent material.

In this embodiment test membrane 2 simultaneously acts as an absorbing pad and liquid is absorbed directly into said membrane. The advantage of this solution is the simplicity of structure and the fact that liquid flow is not dependent on the flow connection between absorbing pad and test membrane. Cover 6 and/or pad 3 may also have an extension equal to backing 1, in which case liquid is absorbed into test membrane 2 through its exposed edges.

In use it is important to avoid dipping the zones of the test membrane into the sample liquid. The reactions may only occur while the liquid front is proceeding along the membrane. Consequently, the depth of dipping should be indicated to the user and most preferably a mark indicating the dipping level is marked on the test strip itself.

One way of performing the test is to dip the receiving end of test strip 10 into a sample up to a marked line until absorbing pad 3 in said receiving end has absorbed a sufficient amount of liquid; immediately thereafter the test strip can be removed from the sample and set aside until the lines have appeared.

In order to ensure an undisturbed migration of the liquid front in the test membrane, it is preferable to use a membrane which has been treated with suitable substances that facilitate liquid uptake (e.g. a detergent like Tween 20, manufactured by BioRad Laboratories, USA) and that cause a suitable electrical charge in relation to the migrating particles (e.g. buffering ions). An untreated membrane may also be treated before dispensing the test specific zones thereto by dipping said membrane into suitable solutions and by drying it thereafter.

Reagents, such as those mentioned above that have an effect of improving test functions, may also be added by drying them into absorbing pad 3 or into the receiving end of test membrane 2. Release of the label particles from said membrane by the liquid flow can be facilitated by drying a suitable mixture, such as a sugar solution underneath the particle zone. The structure of the preferred test strips according to the present invention, wherein absorbing pads and an absorbing membrane are provided between a cover and a backing so that the absorbing edges are open, enables a simple performance of the test. The sample need not be pipetted into the test since absorption is unhampered as the strip is dipped into the liquid. At the chamber-like space formed by the narrow gap 4 in the strip, the flow is sheltered from disturbance and from drying caused by air draught.

It is obvious that test strips according to the present invention may be prepared one by one using pre-cut parts of the right size. However, owing to the test strip according to the invention having a laminated structure which is open at its edges, it has been possible to develop an industrial manufacturing method that is quick, automatic and cost effective. Thus, the test membrane with its reagent zones may be pre-manufactured in a special production line and thereafter the test strip may be assembled in another production line by laminating the various components of the strip into a long test strip band.

The test membrane is preferably manufactured in a production line, where a roll of test membrane material is unreeled, treated and reeled again into a test membrane roll. The reagents needed on the test membrane are dispensed and dried as continuous lines on the membrane material. In this way the sensitive test membrane will be treated in as few mechanical steps as possible and will be protected from damage. Successful and consistent reagent dispensing on the membrane can be observed and ascertained simply by monitoring the width of the reagent line passing under an optical detection instrument. A uniform reagent dispensation is important for reliable test performance. Since the manufacturing technique is fast, the test membrane will remain for only a very short time under the influence of uncontrolled disturbing factors, such as there may exist in ambient air.

All the materials for the assembly of the test strip are advantageously chosen so that they are available in the form of rolls. The production line of the test strip is planned so as to feed the various materials, including test membrane, from rolls in the correct order to be laminated one on top of the other, for example by gluing.

In a typical production method glue, adhesive tape or the like is applied on the band of backing that is fed from a roll of backing material. After that the pad materials are fed from their rolls onto predetermined areas of the backing band at a distance from each other so that a gap will remain between them. Especially the pad material that is to form the pad at the receiving end may be pre-treated with substances that improve liquid flow. Said pad material may also be provided with a test specific reagent. The pre-treated test membrane material is unreeled from its roll and placed in such a position on top of and between the pad material strings. Said membrane may have a protective layer on one side, in which case the side having the reagents exposed should be facing said gap. A transparent plastic band is finally fed from a roll of covering material and attached to the combination of membrane and pads, on said backing. The cover material is adhered to the pad material strings and also to the test membrane material at least at its ends. Finally, the laminate is evenly pressed to ensure adhesion.

Since the production line functions continuously, the homogeneous quality of every single test strip can be easily monitored. It is, for instance, possible to check that mechanical tolerances are met. The production line can easily and quickly be adjusted to fit the requirements of different tests by changing the reagents and/or the width of the material rolls used for lamination.

The long test strip blank produced after lamination is cut into test strips of desired width at the end of the test strip production line. The fresh sections resulting from said cutting will ensure that the edges of the absorbing pads are of homogeneous quality and, consequently, that a sample will be reproducibly and uniformly absorbed. This, in turn, will have a favourable effect on test result precision.

The finished test strips may be packed in the traditional way in single packages (for instance, pouches of plastic laminate containing a bag of moisture binding material). However, since the structure of the test strips according to the invention is light and small, said strips may also be advantageously packed in, for instance, cylinder-like tubes such as aluminum tubes that are impermeable to moisture, tough and easy to handle.

The test strip according to the present invention may be used for instance for pregnancy tests. The test can be designed to be performed directly on urine or serum and the analyte to be determined would be human chorionic gonadotropin (hCG) secreted by the placenta.

The test strip may, however, be adapted also for many other diagnostic tests where the presence or absence of some particular compound is detected in the sample, said compound being connected to a disease or a pato-physiological state or being artificially introduced into the body. This kind of a ± test is especially suitable for diagnosis of infections caused by microbes.

The sample may be liquid such as serum, when showing the presence of rheumatoid factors in rheumatic disease, or urine, when showing the presence of albumin leakage that is caused by damaged kidneys, or spinal fluid, when showing the presence of bacteria causing meningitis. The sample may also be mucous or solid, in which cases the compound to be tested is first extracted in a suitable liquid. An example of an adaptation like this is the detection of Chlamydial antigens in a sample that has been taken from the mucous membranes in a patient's urogenitals. Correspondingly, a sample can be taken from the mucous membranes in the throat in order to detect for example, Streptococcus A. Occult blood in faeces, which is connected to intestinal cancer can be detected in a faecal sample using a test strip according to the invention to show the presence of human hemoglobin in said sample. The presence of Pneumococcus causing pneumonia can be detected in a sputum sample. The rupture of fetal membranes can be detected by showing the presence of a protein called IGFBP-1 in a vaginal secretion sample. If two different label concentrations of a monoclonal antibody against IGFBP-1 are used in the same test, it is possible to detect a low IGFBP-1 concentration connected to susceptibility to delivery or a high concentration caused by rupture of the membranes. It is also possible to show the presence of antibodies connected to infections, such as IgG class antibodies against Helicobacter pylori in serum. Said bacteria have been found to be an important etiologic factor in gastric ulcer.

The test strip according to the present invention may also be adapted for many tests of environmental analysis. The present test strip provides several advantages compared to traditional methods. The test is rapid, inexpensive and easy. There is no prior art way of performing tests of similar sensitivity and specificity in just a few minutes. Test performance itself does not require any specialized equipment and the staff needs no special training. Sample pre-treatment is considerably simpler than what is necessary in most traditional methods. The specificity of an immunochemical method is based on the specificity of antibodies and, therefore, no particular sample cleaning step is needed. It is sufficient that the sample is transformed into liquid form.

There are analytes that are not well adapted for determinations using traditional chromatographic and other corresponding methods, but which are well suited for immunologic techniques (for instance, all proteins). Therefore the present invention offers a possibility for entirely new tests.

Since the tests are cheap and easy to perform, a sufficient number of tests can be done for instance in order to examine a polluted area thoroughly and to monitor the situation for a sufficient length of time. A large enough sampling can be done in foodstuff. The owner of a greenhouse can follow the soil getting cleaned of pesticides (at present there is no other way than to wait for a time that is supposed to be long enough). Even small scale manufacturers of food can have a good follow-up of foodstuff purity.

Using the test strip according to the present invention screening systems of various kinds can be developed. A rapid test can be designed, for instance, to detect a certain group of substances ("polyaromatic hydrocarbons", aflatoxins etc.), the samples being then further analyzed for various components with a more complex laboratory method, if there has been a positive result in a screening test performed on site. A rapid screening of a single analyte can also be performed using a qualitative test (by showing that the concentration is higher than an acceptable limit) and exacter testing may then be carried out using a slower but more sensitive quantitative laboratory method, if a positive screening result has been obtained.

Suitable environmental adaptations of the test strip according to the present invention that are worth while mentioning are, for instance, the screening of areas with polluted soil and water in order to find out their PCP or PCB concentrations or to detect aromatic or chlorinated aliphatic hydrocarbons. In industrial areas possible releases of various chemicals, such as, for instance, oil compounds, solvents and pesticides can be monitored. Occurrence of various toxins, antibiotics, histamine, micro-organisms or pesticides can be studied in foodstuff. Carcinogenic compounds like benzopyrene can be determined in escaping gas. Toluene and related compounds containing aromatic ring structures that are used as markers for petroleum fuel can be detected in contaminated soil.

The following examples illustrate the present invention without, however, limiting it in any way.

EXAMPLE 1

Pregnancy test

Label preparation: In order to prepare a test strip according to the invention, blue latex particles were coated with a monoclonal antibody against hCG. The size of the particles was 200 nm. The detection label made in this way was stored as a 1% suspension in a buffer.

Test membrane preparation (alternative 1): The material used to prepare a test membrane was nitrocellulose that had been attached to a thin transparent plastic backing. The membrane was 30 mm long. Sugar solution was dried in a zone 9 mm from one end of the membrane, and thereafter, the label described above was dispensed on the dry sugar zone. A second narrow zone was dispensed 18 mm from said end of said membrane, said second zone containing a solution of another monoclonal antibody to hCG in a buffer. A third narrow zone was dispensed 2 mm from the second zone, said third zone containing antibodies to mouse immunoglobulin.

Test membrane preparation (alternative 2): The same material as in alternative 1 was used but only the second and third zones were dispensed on it. The latex label of said first zone was instead dried into an absorbing pad used at the receiving end of the test strip.

Assembly of the test strip: A white polyester sheet was cut into pieces of 6 mm×120 mm size to prepare backing supports for the test strip. The material used to prepare the absorbing pads at both ends of the test strip was rayon fiber in about 1 mm thick layers between two polyethylene tissues. A 30 mm piece of pad material was attached to the receiving end of the backing support and, correspondingly a 70 mm piece was attached to the opposite end. In alternative 2 the receiving end pad had been provided with the label reagent. The dried test membrane prepared as described above was placed on top of the pads so that it overlapped both pads for about 5 mm at either end. The coated nitrocellulose side was facing downwards towards an empty chamber-like gap formed between pads, backing and membrane. A covering support sheet of transparent polyester was cut into pieces of the size of the backing. The cover was attached to the pads and partly also to the membrane along a few millimeters thereof. Nontransparent tape was attached to both ends of the cover so that only a 10 mm wide space remained uncovered at the site where the specific line and the control line were formed.

Some test strips were assembled so that the test membrane was attached to the backing support in such a way that the reactive nitrocellulose side was facing upwards. Pads were placed in contact with either end of the test membrane in a way corresponding to that described above. Again, a transparent cover was attached on top. No gluing was done on the nitrocellulose surface. The difference of the result compared to the assembly described above was that the chamber-like gap was formed above the membrane and not under it.

Performance of the pregnancy test

1. The receiving end of the test strip was dipped 20 mm deep into a sample.
2. The strip was removed from the sample.
3. After 5 minutes, the number of blue lines appearing in the test strip was recorded and the result was interpreted.

Interpretation of the result:

Such an amount of antibody had been applied in the specific line that a hCG concentration of about 50 IU/l would be the lowest that could cause enough label to bind so that a visible line would appear and the test be interpreted as positive. The antibody against mouse immunoglobulin that had been applied to the control line would unspecifically bind the label carried by the liquid flow, since the label was coated with a mouse antibody belonging to class IgG. The solutions were added in such ratios that even if the concentration of hCG were high, there would be a sufficient amount of label that would not bind to the specific line so that a visible control line would form, indicating that the liquid flow had proceeded in a proper manner and the test was functioning. The appearance of a blue control line showed that the test had worked in a reliable way.

The results of a test series are presented in Table 1 below. Known amounts of hCG had been added into a sample that was known to be negative.

TABLE 1

| Concentration hCG in sample (IU/l) | Specific line | Control line | Interpretation |
|---|---|---|---|
| 0 | − | + | negative |
| 25 | − | + | negative |
| 100 | + | + | positive |
| 1000 | + | + | positive |
| 10000 | + | + | positive |
| 100000 | + | + | positive |
| 200000 | + | + | positive |

The test strips wherein the membrane was attached to the backing support gave an identical result.

EXAMPLE 2

A test to detect the rupture of fetal membranes

The test to detect the rupture of fetal membranes was based on an indication of the presence of IGFBP-1 (Insulin-like growth factor binding protein-1) in a sample of vaginal secretion. The label, the test membrane and assembly of the test strip were performed in the same way as in Example 1, except that since the protein to be determined was IGFBP-1, the antibodies used in the label and in the specific line were monoclonal antibodies to IGFBP-1.

Sample: A sample of vaginal secretion was taken with a sterile dacron swab. The sample that had been absorbed into the swab was extracted in a dilution buffer in a predetermined ratio.

Performance of the test:

1. The receiving end of the test strip was dipped 20 mm deep into the sample extract.

2. The strip was removed from the sample.

3. After 5 minutes, the number of blue lines appearing in the test strip was recorded and the result was interpreted.

The results of a test series are presented in Table 2 below. Amniotic fluid had been diluted in a salt solution (the concentration of IGFBP-1 in the amniotic fluid sample was known).

| IGFBP-1 (µg/l) | Specific line | Control line | Interpretation |
|---|---|---|---|
| 0 | − | + | negative |
| 20 | − | + | negative |
| 200 | + | + | positive |
| 500 | + | + | positive |
| 1000 | + | + | positive |
| 50000 | + | + | positive |

In the test dilution used, an IGFBP-1 concentration of 200 µg/l can be considered to be so high that in a vaginal secretion sample it can only be caused by the presence of amniotic fluid and can be interpreted to indicate that the fetal membranes have ruptured.

EXAMPLE 3

A test to detect occult blood in faeces (two analytes)

This test is meant to detect blood in faeces which occurs after bleeding in the intestines in cancer patients. The test was designed to be based on showing the presence of both human hemoglobin and human albumin. Hemoglobin is a more specific marker of blood because albumin can enter faeces as a result of a protein leakage that is not in connection with cancer. Albumin, in turn, is more stable in faeces than hemoglobin. The label, the test membrane and the assembly of the test strip were performed in the same way as in Example 1, except that since two analytes are to be detected, a mixed label was prepared which contained particles coated with a hemoglobin antibody as well as particles coated with an albumin antibody. Correspondingly, also two different specific lines were applied on the membrane. When applying them it was taken into account that the test must be as sensitive as possible.

The sample: A small sample of faeces was suspended in a buffer solution. The suspension, which should be as homogenous as possible, was filtered and the filtrate was transferred into a test tube.

Test performance:

1. The receiving end of the test strip was dipped 20 mm deep into the filtrate.

2. The strip was removed from the sample.

3. After 5 minutes, the number of blue lines appearing in the test strip was recorded and the result was interpreted.

One line meant that the test was negative, three lines meant that it was positive. If only two lines have appeared it is recommended that a new sample is taken.

EXAMPLE 4

A test for detecting toluene in soil

Antibody preparation: Murine monoclonal antibodies against toluene are developed using methods known to those skilled in the art (see for example, Stenman U. -H. et al.; *J. Immunol. Methods* 1981; 46: 337–345). The nature of the antigen being a hapten it is required that mice are immunized with an antigen derivative of larger molecular weight. Therefore, tolylacetic acid is covalently conjugated to bovine serum albumin (BSA) for immunizations (for conjugation and use of conjugates in immunization, see: Muller S., *Laboratory Techniques in Biochemistry and Molecular Biology*, Vol. 19, eds Burdon R. H. and van Knippenberg P. H., Elsevier, Amsterdam 1988, p. 95–130, or Hudson L. and Hay F. C., *Practical Immunology*, Blackwell, Oxford 1983, p. 1–23). For antibody screening, a radio immunoassay is used.

The radioactive label needed in the method is prepared as follows: tolylacetic acid is conjugated to a carrier peptide containing at least one tyrosine residue (for conjugation, see above) and the conjugate is radio iodinated using a standard Chloramine T method. The obtained monoclones reactive with toluene are tested for cross-reactions with related compounds found in fuels. In this case, cross-reactions are not harmful, but desirable, since the antibodies are intended to be used in a test where any marker of fuel contamination may cause a positive result.

Test strip preparation: The label, the test membrane and test strip assembly are performed as described in Example 1, except that the specific line in the membrane is prepared by coating with antigen (tolylacetic acid-carrier peptide conjugate) instead of a second antibody. The antibody attached to the label particles is monoclonal anti-toluene.

Sample preparation: A sample material of standard weight is extracted with a known volume of methanol. The extract is diluted with diluent buffer in a predetermined ratio of volumes (at least 1:5) and used as sample in the test.

Test performance

1. The receiving end of the test strip is dipped 20 mm deep into the sample liquid.

2. The strip is removed from the liquid.

3. After 5 minutes, the number of blue lines appearing in the test strip is recorded and the result is interpreted.

Interpretation: The test is based on a competitive principle. Antigen in the sample will compete for the binding sites of label antibody with antigen in the specific test line. The amount of antibody in the label is adjusted so that even a very low amount (corresponding about 5 ppm or more in the original sample) of toluene or a toluene related compound found in petroleum fuel will block the binding sites and no blue specific line can be formed on the strip. Therefore, if two blue lines have appeared, the test can be interpreted as being negative. If only one blue line (the control line) has appeared, the test is positive and the soil sample is contaminated.

EXAMPLE 5

A test for detecting Salmonella sp. in food

Antibody preparation: Murine monoclonal antibodies against Salmonella are developed using methods known to those skilled in the art (see for example, Stenman U. -H. et al., *J. Immunol. Methods*, 1981;46: 337–345). Salmonella sp. cell wall extract is used as antigen in immunizations. For antibody screening, an ELISA method is used where microwell plates are coated with the same cell wall extract. Antibodies attached to the antigen coated surface are detected with enzyme (HRP, horseradish peroxidase)

labelled rabbit anti-mouse immunoglobulin. The clones that are found positive are then tested with ELISA methods using cell wall extracts of other major pathogenic Salmonella species. A broad group specificity is desired. The selected monoclones are tested for cross-reactions to exclude harmful reactions with other bacteria known to be common in foodstuff.

Test strip preparation: The label, the test membrane and test strip assembly are performed as described in Example 1. Monoclonal Salmonella antibodies are coated on the label particles and the specific line on the test membrane.

Sample preparation: An enrichment culture is performed on the food specimen and culture medium diluted with assay buffer favourable to antigen exposure is used as sample in the test. When heavy Salmonella contamination is to be expected, the test can be performed without enrichment by diluting the original specimen, if it is liquid, or can be suspended in liquid form.

Test performance

1. The receiving end of the test strip is dipped 20 mm deep into the sample liquid.

2. The strip is removed from the sample.

3. After 5 minutes, the number of blue lines appearing in the test strip is recorded and the result is interpreted.

Interpretation: If one blue line has appeared in the strip, the result is negative. If two blue lines have appeared, the test is positive for Salmonella sp. The test can detect 0.1–1 million bacteria/ml or more.

Above, the invention has been explained with reference to certain embodiments in diagnostic and environmental testing. It should be clear that said examples are only illustrative, and that a person skilled in the art will be able to vary the invention within the limits set by the appended claims, without deviating from the scope of the present invention.

We claim:

1. A test strip for a rapid immunoassay which comprises a backing member having positioned thereon a receiving end pad and a finishing end pad located a distance downstream of said receiving end pad, a test membrane being provided on and in liquid flow contact with said pads such that said backing member and said test membrane are in a spaced apart relationship to define top and bottom boundaries of an air gap therebetween, said test membrane having thereon at least one immunochemical reagent zone and being positioned in parallel relationship to said backing member, whereby said air gap is open at its edges in a direction perpendicular to said downstream direction.

2. A test strip according to claim 1 wherein said receiving end pad and said finishing end pad are of a liquid absorbing material.

3. A test strip according to claim 1 or 2, wherein a cover which has at least one transparent portion is positioned over said pads and said test membrane said at least one transparent portion being positioned over said at least one immunochemical reagent zone of said test membrane.

4. A test strip according to claim 3 wherein said test membrane is made of a porous material and being at least partly adhered to said backing member or to said cover.

5. A test strip according claim 3 wherein said receiving end pad or said membrane contains one or more label zones containing movable colored particles coated with an immunochemical reagent, and wherein said at least one immunochemical reagent zone is positioned on said test membrane within the area corresponding to said air gap and comprises at least one test zone containing immobilized immunochemical reagents, and at least one control zone containing immobilized immunochemical reagents for indicating proper flow conditions.

6. A test strip according to claim 5 wherein said label zones contain different specific immunochemical reagents for more than one analyte to be tested and/or different concentrations of one or more specific immunochemical reagents.

7. A test strip according to claim 5 wherein said label zone contains colored particles coated with antibodies comprising
    (a) monoclonal hCG antibody,
    (b) monoclonal IGFBP-1 antibody,
    (c) both hemoglobin antibody and albumin antibody,
    (d) monoclonal anti-toluene, or
    (e) monoclonal Salmonella antibody,
and that said test zone contains
    (a) another monoclonal hCG antibody,
    (b) another monoclonal IGFBP-1 antibody,
    (c) another hemoglobin antibody and another albumin antibody,
    (d) a toluene conjugate, or
    (e) monoclonal Salmonella antibody, respectively.

8. A process for manufacturing a test strip according to claim 1, which comprises the steps of
    (a) longitudinally dispensing and drying at least one continuous zone of at least one immunochemical reagent onto a continuous length of test membrane,
    (b) attaching at least two separate continuous strings of pad material at a distance from each other onto a continuous length of backing material,
    (c) placing the length of test membrane prepared in step (a) onto said strings of pad material so that said at least one reagent zone is aligned with a gap formed between said strings of pad material,
    (d) attaching a continuous length of transparent cover material onto said pad strings and said membrane length, and
    (e) cutting the resulting strip blank into test strips of a desired size.

9. A process according to claim 8, wherein two or more separate continuous zones of reagents are dispensed and dried onto said length of membrane.

10. A test strip according to claim 1, wherein said at least one immunochemical reagent zone comprises immobilized immunochemical reagents specific for one or more environmental analytes.

11. A test strip according to claim 1, wherein said at least one immunochemical reagent zone comprises immobilized immunochemical reagents specific for one or more diagnostic analytes.

12. A test strip according to claim 4, wherein said porous material is nitrocellulose or nylon.

13. A test strip according to claim 5, wherein said immunochemical reagent is an antibody.

14. A process according to claim 8, wherein one or more continuous zones of label reagent are dispensed and dried onto one of said strings of pad material.

* * * * *